United States Patent [19]

Dolhyj et al.

[11] Patent Number: 4,508,848

[45] Date of Patent: Apr. 2, 1985

[54] CATALYSTS AND PROCESS OF MAKING

[75] Inventors: Serge R. Dolhyj, Parma; Roseann M. Enyedy, Brecksville, both of Ohio

[73] Assignee: The Standard Oil Company, Cleveland, Ohio

[21] Appl. No.: 540,595

[22] Filed: Oct. 11, 1983

[51] Int. Cl.³ .................. B01J 21/06; B01J 21/00; B01J 23/16
[52] U.S. Cl. .................................. 502/239; 502/242; 502/246; 502/351; 502/353
[58] Field of Search ............... 502/239, 242, 247, 351, 502/353

[56] References Cited

U.S. PATENT DOCUMENTS

| | | | |
|---|---|---|---|
| 3,106,569 | 10/1963 | Robinson et al. | 502/242 X |
| 4,075,231 | 2/1978 | Dolhy et al. | 502/204 X |
| 4,076,731 | 2/1978 | Dolhyj et al. | 502/202 X |
| 4,162,992 | 7/1979 | Wise | 502/242 |

*Primary Examiner*—Carl F. Dees
*Attorney, Agent, or Firm*—Charles S. Lynch; John E. Miller, Jr.; Larry W. Evans

[57] ABSTRACT

Disclosed are vanadium-antimony oxide catalysts deposited as an outer layer on certain oxide support compositions. A method of making a microspheroidal fluidizable catalyst of such description is disclosed. The catalysts are useful for the oxidative conversion of o-xylene to phthalic anhydride and have good attrition resistance, as well as good activity for such reactions.

21 Claims, No Drawings

CATALYSTS AND PROCESS OF MAKING

The present invention relates to catalysts suitable for oxidation of o-xylene to phthalic anhydride. In a particular aspect the invention relates to catalytic vanadium-antimony oxide catalysts deposited as an outer layer on certain oxide support compositions, particularly in microspheroidal, fluidizable form. In another aspect the invention relates to a method of making a fluidizable catalyst having both good attrition resistance and activity for catalyzing the oxidation of o-xylene to phthalic anhydride.

In prior U.S. Pat. Nos. 4,075,231 and 4,076,731 there are described catalysts having a particle size of at least about 20 microns and containing vanadium and antimony in oxide form coated onto a support material such as silica, alumina, titania or alumina-silica. The coating was applied by the wet coating method whereby the solid particulate support material was wetted and then active oxide powdered materials were coated onto the surface of the support, the composite dried and then activated by further heating at elevated temperature.

We have found that a vanadium oxide microspheroidal catalyst for use in a fluidized catalytic system needs to be promoted with antimony oxide for suitable activity and that it is important also that the overall catalyst contain $TiO_2$ to enhance catalytic activity for making phthalic anhydride from o-xylene. However, we have also found that a microspheroidal catalyst of the present composition but made by the "wet coating" method of the aforementioned patents is entirely unsatisfactory because of non-uniformity, as discussed with respect to the specific examples herein.

Catalysts made by the conventional technique of making a slurry of the components—or a solution/slurry—and then spray drying have good activity but such low resistance to attrition as to be completely impractical for use in a fluidized bed.

It is an object of the present invention to provide a method for preparing a particulate catalyst comprising a vanadium-antimony oxide catalyst on a support of silica, silica-alumina or alumina, which base also contains $TiO_2$ wherein the catalytic components are more uniformly coated on the base than in the prior art wet coating method.

It is a further object to provide such a method wherein the resulting microspheroidal catalyst has good attrition resistance under fluidization conditions.

A still further object is to provide the superior attrition resistant catalyst resulting from the foregoing process.

Another object is to provide a new catalyst suitable for oxidation of o-xylene to phthalic anhydride, and a process using such catalyst.

Other objects, as well as aspects, features and advantages of the invention, will be apparent from a study of the specification, including the examples and claims.

According to one aspect of the invention there is provided a composite complex oxide catalyst comprising (1) a particulate support containing Si or Al, or both, Ti in the ratios represented by the empirical formula $TiSi_nAl_mO_x$, wherein n is a number from 0-5, m is a number from 0-6, n+m=0.4 to 6 and x is the number of oxygens required to satisfy the valence requirements of the other elements present; and (2) coated on the outer surface of said support a catalytic metal oxide composition containing vanadium and antimony wherein the atomic ratio of vanadium to antimony is in the range from 1:3 to 1:7 and the oxygen is present in the amount to satisfy the valence requirements of the other elements present in said coating, and wherein the weight ratio of (2) to (1) is in the range from 1:50 to 3:7, usually 1:12 to 1:4. Usually n is in the range from 1-2, m is in the range from 1-2 and n+m is in the range from 1-2.

The catalysts of the present invention, or made by the process of the invention, are particularly useful for the oxidation of o-xylene to phthalic anhydride.

According to the present invention such a catalyst preferably is the result of a process comprising coating dry powders of vanadium oxide and antimony oxide onto the outer surface of the particulate support in dry form after it has been calcined at an elevated temperature, and thereafter calcining the resulting composite. Such a catalyst made in microspherical fluidizable sizes (passing though a No. 70 U.S. Standard Sieve Series screen) is particularly attrition resistant when used in a fluidizable bed conversion reaction, in contrast to the prior art slurry method mentioned hereinbefore. Further, attempts to make a satisfactory, evenly coated catalyst of the present composition by the wet coating method of the prior art patents cited herebefore give unsatisfactory results as earlier discussed.

The shortcomings of these prior art approaches are surprisingly overcome according to the process aspect of the invention which comprises making a microspheroidal fluidizable catalyst having a substantially even coating on a microspheroidal support or base, which comprises the steps of:

(1) forming a microspheroidal support material having Ti and having Si or Al, or both, in the ratios represented by the empirical formula $TiSi_nAl_mO_x$, wherein n is from 0 to 5, m is from 0 to 6, and n+m is in the range from 0.4 to 6, and x is the number of oxygens required to satisfy the valence requirements of the other elements present, (usually each of n and m are 1 to 2 and n+m is 1 to 2), by spray drying an aqueous dispersion containing $TiO_2$, and $SiO_2$ or $Al_2O_3$, or both, (2) calcining said microspheroidal support at a temperature in the 750° to 1000° C., usually 850° to 950° C., (3) dry coating a mixture containing dry powders of vanadium oxide and antimony oxide, wherein the atomic ratio of vanadium to antimony in said mixture is in the range from 1:3 to 1:7, onto dry microspheroidal support material resulting from step (2), the weight ratio of said antimony and vanadium oxides coated onto said support material being in the range from 1 part of said oxides per 50 parts of support to 3 parts of said oxides per 7 parts of support, more usually 1 part of the combined antimony and vanadium oxides to from 4 to 12, inclusive, parts of said support material, and (4) calcining the resulting composite coated microspheroidal material at a temperature in the range from 600° to 800° C., usually from 675° to 775° C.

In a still further aspect of the present invention o-xylene is oxidized to phthalic anhydride by contacting a mixture of a gas containing $O_2$ and vaporous o-xylene with a catalyst of the invention or made according to the process of the invention. In the case of the microspheroidal fluidizable catalysts the o-xylene and molecular oxygen containing gas are passed through a fluidized bed of the catalyst at temperatures in the range from 200° to 600° C., usually 300° to 500° C. Normally air is employed to supply the $O_2$, and the air/xylene volume ratio is usually from about 30 to 130 or more. The reaction can be effected at atmospheric or above or below atmospheric pressure although nearly atmospheric pressure is usually used.

Reference to attrition tests in this application are to a standard test carried out as follows: A two chamber fluidizing attrition vessel is used. The bottom cylindrical chamber is 1.5 in. I.D. and 27.5 in. high. It communicates with the top chamber that is 22 in. high and 5 in. I.D. The top chamber is also cylindrical, but the bottom 4 inches of it is funnel shaped, tapering down to meet the top of the bottom chamber.

The 50 gram sample to be tested for attrition was placed in the vessel. The part of the catalyst sample tested was that passing through a 140 mesh (U.S. Standard Series) screen and retained on a 230 mesh screen. In the examples of the invention no fines of initial catalyst passed through the 230 mesh screen. In the bottom of the bottom chamber were 3 sapphire tipped jets, each 0.015 in. I.D., through which air was introduced upwardly at the rate of 15 cu. ft. per hour. Any fines formed by attrition passed from a top opening of the upper chamber and were collected, and the total fines weighted after 5 hours and after 20 hours. This weight divided by the initial 50 grams × 100 gives the weight percent lost to fines by attrition after 5 and 20 hours.

When "microspheroidal" supports or catalysts are referred to herein the size of the spheroids is intended to include only spheroids that pass a No. 70 screen (U.S. Standard Sieve Series).

When reference is made in the claims to the aqueous dispersion of $TiO_2$, and $SiO_2$ or $Al_2O_3$, or both, for the spray drying step, it is to be understood that the oxides are not necessarily always, strictly speaking, oxides per se; for instance, the dispersion may contain a silica sol which has some OH groups. In any event the dispersion is of sols or of slurried components or many contain truly dissolved species, and the materials present are such that after spray drying and calcination they are in oxide form.

The following examples are representative only and should not be taken as limiting the scope of the invention.

EXAMPLE 1

Equal weight amounts of powdered anatase and colloidal $SiO_2$ (Nalco 2329) were slurried in water, the slurry spray dried and calcined in air at 900° C. for 5 hours to make the support in microspheroidal form. The material was essentially, all microspheroidal without fines (any material that passes through 325 mesh), and the attrition resistance (or loss) test showed less than 3 percent was lost as fines when the test was run for 20 hours for the resulting $TiSi_{1.33}O_{4.66}$ microspheroids.

145.75 g. of $Sb_2O_3$ and 18.19 g. of $V_2O_5$ were ball milled together and formed an intimate, essentially homogeneous material. It was screened and all passed through No. 200 screen, U.S. Sieve Series.

18 g. of the $V_2O_5Sb_2O_3$ powder were mixed with 102 g. of the microspheroidal $TiSi_{1.33}O_{4.66}$ by rolling in a cylindrical jar on a ball mill roller. The mixture had a homogeneous appearance and microscopic examination showed that the vanadium-antimony oxide mixture was uniformly coated on the $SiO_2/TiO_2$ substrate microspheres.

The coated microspheres were calcined in air by heating at 750° C. for 5 hours.

The catalyst was tested for attrition resistance. Total production of fines was 1.8 weight percent after 5 hours and 3.7 percent after 20 hours. After this test the catalyst was essentially all uniformly coated microspheres.

The catalyst was used to convert o-xylene to phthalic anhydride by oxidation in air. To carry out the reaction an 8 inch tall, ⅜ inch I.D. tubular reactor having 6 sieve trays spaced ½ inch vertically from each other was used. The reactor was heated in a salt bath and had a thermowell for temperature measurement. Air and liquid o-xylene were separately introduced into the bottom of the tube below the lowest sieve tray. The reactor contained 40 cc of microspheroidal catalyst (on an unexpanded basis) which was fluidized by the flow of the gases. The ratio of air to o-xylene was 40/1 and the contact time (based on unexpanded catalyst) was 5.1 seconds. The salt bath was at 350° C. and the peak exothermic temperature in the reactor was 368° C. The per pass conversion to phthalic anhydride was 46 percent and the total conversion of o-xylene was 84 percent.

EXAMPLE 2

When a catalyst was made as in Example 1 except that the final catalyst was calcined at 427° C. instead of 750° C., it was inactive, converting only 0.2 percent of the o-xylene to phthalic anhydride when it was attempted to repeat the reaction as in Example 1.

EXAMPLE 3

When it was attempted to make the catalyst of Example 1 by the wet coating method of U.S. Pat. Nos. 4,076,731 and 4,075,231, the final calcined catalyst was non-uniform and contained particles of the vanadium-antimony oxide, poorly coated $TiSi_{1.33}O_{4.66}$ support and substantially uncoated support particles. Such a catalyst would be entirely unsatisfactory, and the various types of particles would have different rates of attrition and would thus change in composition during use.

EXAMPLE 4

Equal weight amounts of powdered rutile and colloidal $SiO_2$ (Nalco 2329) were slurried in water, the slurry spray dried and calcined in air at 900° C. for 5 hours to make the support in microspheroidal form. The material was essentially all microspheroidal without fines (any material that passes through 325 mesh), but some of the microspheres were clustered. The empirical formula of the support was $TiSi_{1.33}O_{4.66}$.

80 parts by weight of $Sb_2O_3$ and 10 parts by weight of $V_2O_5$ were ball milled together and formed an intimate, essentially homogeneous powder material. It was screened and all passed through No. 200 screen, U.S. Sieve Series.

15 parts by weight of the $V_2O_5/Sb_2O_3$ powder were mixed with 85 parts by weight of the microspheroidal $TiSi_{1.33}O_{4.66}$ by rolling in a cylindrical jar on a ball mill roller. The mixture coated fairly evenly on the support, although not quite as well as in Example 1.

The coated microspheres were calcined in air by heating at 750° C. for 5 hours.

The microspheroidal catalyst resulting was tested for attrition resistance. Total production of fines was 15.3 weight percent after 5 hours and 23.1 percent after 20 hours, not as good as Example 1, but better than in Example 6, made by the conventional slurry method.

The catalyst was used to convert o-xylene to phthalic anhydride by oxidation in air. To carry out the reaction an 8 inch tall, ⅜ inch I.D. tubular reactor having 6 sieve trays spaced ½ inch vertically from each other was used.

The reactor was heated in a salt bath and had a thermowell for temperature measurement. Air and liquid o-xylene were separately introduced into the bottom of the tube below the lowest sieve tray. The reactor contained 40 cc of microspheroidal catalyst (on an unexpected basis) which was fluidized by the flow of the gases. The ratio of air to o-xylene was 40/1 and the contact time (based on unexpanded catalyst) was 5.4 seconds. The salt bath was at 310° C. and the peak exothermic temperature in the reactor was 321° C. The per pass conversion to phthalic anhydride was 69 percent and the total conversion of o-xylene was 99 percent.

EXAMPLE 5

Equal weight amounts of powdered anatase and colloidal $SiO_2$ (Nalco 2329) were slurried in water, the slurry spray dried and calcined in air at 900° C. for 5 hours to make the support in microspheroidal form. The material was essentially all microspheroidal without fines (any material that passes through 325 mesh), and the attrition resistance (or loss) test showed less than 3 percent was lost as fines when the test was run for 20 hours for the resulting $TiSi_{1.33}O_{4.66}$ microspheroids.

80 parts by weight of 10 parts by weight of $Sb_2O_3$ and 10 parts by weight of $V_2O_5$ were ball milled together and formed an intimate, essentially homogeneous material. It was screened and all passed through No. 200 screen, U.S. Sieve Series.

5 g. of the $V_2O_5/Sb_2O_3$ powder were mixed with 45 g. of the microspheroidal $TiSi_{1.33}O_{4.66}$ by rolling in a cylindrical jar on a ball mill roller. The mixture had a homogeneous appearance and microscopic examination showed that the vanadium-antimony oxide mixture was uniformly coated on the $SiO_2/TiO_2$ substrate microspheres.

The coated microspheres were calcined in air by heating at 750° C. for 5 hours. The catalyst was mostly good uniform microsperoids with no dust or powder.

The catalyst was used to convert o-xylene to phthalic anhydride by oxidation in air. To carry out the reaction an 8 inch tall, ⅞ inch I.D. tubular reactor having 6 sieve trays spaced ½ inch vertically from each other was used. The reactor was heated in a salt bath and had a thermowell for temperature measurement. Air and liquid o-xylene were separately introduced into the bottom of the tube below the lowest sieve tray. The reactor contained 40 cc of microspheroidal catalyst (on an unexpanded basis) which was fluidized by the flow of the gases. The ratio of air to o-xylene was 40/1 and the contact time (based on unexpanded catalyst) was 5.8 seconds. The salt bath was at 365° C. and the peak exothermic temperature in the reactor was 404° C. The per pass conversion to phthalic anhydride was 46 percent and the total conversion of o-xylene was 90.3 percent.

EXAMPLE 6

In this comparative example a vanadium/antimony oxide, $TiO_2/SiO_2$ catalyst was made by the standard slurry technique involving adding 8 parts by weight of $Sb_2O_3$, 18 parts of rutile and 9 parts of $SiO_2$ to an aqueous $NH_4VO_3$ solution equivalent to 1 part by weight of $V_2O_5$, spray drying the slurry, and calcining at 750° C. The attrition test showed that the catalyst was unsatisfactory, with an attrition loss to fines of 39.4 weight percent after 20 hours and much additional powder and broken microspheroids.

As illustrated by Examples 1 and 4, either rutile or anatase (or a mixture) can be used to supply $TiO_2$. In either case a uniformly coated catalyst with good activity, and with better attrition resistance compared to the conventional slurry/spray dried technique results. But anatase gives the best attrition properties while rutile results in a catalyst with somewhat higher activity. Therefore, one practicing the invention has a choice—anatase, rutile or a mixture—depending on results desired.

As will be evident to those skilled in the art, various modifications of this invention can be made or followed in the light of the foregoing disclosure and discussion without departing from the spirit and scope of the disclosure or from the scope of the claims.

We claim:

1. A composite complex oxide catalyst comprising (1) a particulate support containing Si or Al, or both, and Ti in the ratios represented by the empirical formula $TiSi_nAl_mO_x$, wherein n is a number from 0–5, m is a number from 0–6, n+m=0.4 to 6 and x is the number of oxygens required to satisfy the valence requirements of the other elements present; and (2) coated on the outer surface of said support a catalytic metal oxide composition containing vanadium and antimony wherein the atomic ratio of vanadium to antimony is in the range from 1:3 to 1:7 and the oxygen is present in the amount to satisfy the valence requirements of the other elements present in said coating, and wherein the ratio of (2) to (1) is in the range from 1:50 to 3:7.

2. A catalyst of claim 1 wherein the support is calcined in an $O_2$ containing gas at a temperature in the range from 750° to 1000° C., and dry powders of vanadium oxide and antimony oxide are dry coated onto the dry calcined particles of the support and thereafter the resulting composite is calcined at a temperature in the range from 600° to 800° C.

3. A catalyst of claim 2 wherein the support is calcined at a temperature in the range from 850° to 950° C., and the composite is calcined at a temperature in the range from 675° to 775° C.

4. A catalyst of claim 1 wherein each of n and m are 1–2, and n+m is 1–2.

5. A catalyst of claim 1 wherein the ratio of (2):(1) is in the range from 1:12 to 1:4.

6. An attrition resistant microspheroidal fluidizable catalyst of claim 1 wherein essentially all of the catalyst passes through a No. 70 U.S. Standard Sieve Series screen.

7. An attrition resistant microspheroidal fluidizable catalyst of claim 2 wherein essentially all of the catalyst passes through a No. 70 U.S. Standard Sieve Series screen.

8. An attrition resistant microspheroidal fluidizable catalyst of claim 3 wherein essentially all of the catalyst passes through a No. 70 U.S. Standard Sieve Series screen.

9. A catalyst of claim 7 wherein $TiO_2$ and $SiO_2$ or $Al_2O_3$, or both are dispersed in an aqueous medium and spray dried to form said support before it is calcined.

10. A catalyst of claim 8 wherein $TiO_2$, and $SiO_2$ or $Al_2O_3$, or both, are dispersed in an aqueous medium and spray dried to form said support before it is calcined.

11. A catalyst of claim 7 wherein each of n and m are 1–2, and n+m is 1–2.

12. A catalyst of claim 8 wherein each of n and m are 1–2, and n+m is 1–2.

13. A method of making an attrition resistant coated microspheriodal fluidizable catalyst of claim 6 which comprises (1) forming a microspheroidal support material represented by said empirical formula $TiSi_nAl_mO_x$ by spray drying an aqueous dispersion containing $TiO_2$, and $SiO_2$ or $Al_2O_3$, or both, (2) calcining said microspheroidal support at a temperature in the range of 750°–1000° C., (3) dry coating a mixture of powders of vanadium oxide and antimony oxide onto the surface of the dry calcined microspheroidal support material, and (4) calcining the resulting composite coated microspheroidal material at a temperature in the range from 600° to 800° C., so that said support material acquires said surface coating of said catalytic metal oxide composition containing vanadium and antimony.

14. A method according to claim 13 wherein the calcining temperature of step (2) is in the range from 850° to 950° C.

15. A method according to claim 13 wherein the calcining temperature of step (4) is in the range from 675° to 775° C.

16. A method according to claim 14 wherein the calcining temperature of step (4) is in the range from 675° to 775° C.

17. A method according to claim 13 wherein the weight ratio of the coating on the support to the support is in the range from 1:12 to 1:4.

18. A method according to claim 13 wherein each of n and m are 1–2 and n+m is 1–2.

19. A method according to claim 17 wherein the calcining temperature of step (2) is in the range from 850° to 950° C.

20. A method according to claim 17 wherein the calcining temperature of step (4) is in the range from 675° to 775° C.

21. A method according the claim 19 wherein the calcining temperature of step (4) is in the range from 675° to 775° C.

* * * * *